(12) United States Patent
Park et al.

(10) Patent No.: US 11,892,410 B2
(45) Date of Patent: Feb. 6, 2024

(54) METHOD FOR PREPARING SOLID-STATE PHOTONIC CRYSTAL IPN COMPOSITE FUNCTIONALIZED WITH ENZYME, PHOTONIC CRYSTAL IPN COMPOSITE PREPARED BY THE METHOD AND BIOSENSOR USING THE PHOTONIC CRYSTAL IPN COMPOSITE

(71) Applicant: Kyungpook National University Industry-Academic Cooperation Foundation, Daegu (KR)

(72) Inventors: Soo Young Park, Daegu (KR); Kyung Gyu Noh, Daegu (KR)

(73) Assignee: Kyungpook National University Industry-Academic Cooperation Foundation, Daegu (KR)

( * ) Notice: Subject to any disclaimer, the term of this patent is extended or adjusted under 35 U.S.C. 154(b) by 554 days.

(21) Appl. No.: 17/051,631

(22) PCT Filed: Feb. 20, 2019

(86) PCT No.: PCT/KR2019/002039
§ 371 (c)(1),
(2) Date: Oct. 29, 2020

(87) PCT Pub. No.: WO2019/168292
PCT Pub. Date: Sep. 6, 2019

(65) Prior Publication Data
US 2021/0389252 A1 Dec. 16, 2021

(30) Foreign Application Priority Data
Mar. 2, 2018 (KR) .................. 10-2018-0025203

(51) Int. Cl.
| | |
|---|---|
| *G01N 21/75* | (2006.01) |
| *C09K 19/58* | (2006.01) |
| *C12N 11/04* | (2006.01) |
| *C12Q 1/58* | (2006.01) |
| *C12N 9/80* | (2006.01) |
| *C08J 3/075* | (2006.01) |
| *G01N 21/80* | (2006.01) |

(52) U.S. Cl.
CPC ............ *G01N 21/75* (2013.01); *C08J 3/075* (2013.01); *C09K 19/586* (2013.01); *C12N 9/80* (2013.01); *C12N 11/04* (2013.01); *C12Q 1/58* (2013.01); *G01N 21/80* (2013.01); *C08J 2333/08* (2013.01)

(58) Field of Classification Search
None
See application file for complete search history.

(56) References Cited

FOREIGN PATENT DOCUMENTS

| | | |
|---|---|---|
| KR | 10-2004-0066159 A | 7/2004 |
| KR | 10-1825597 B1 | 2/2018 |

OTHER PUBLICATIONS

Lee, Hyun-Gyu, Sundas Munir, and Soo-Young Park. "Cholesteric liquid crystal droplets for biosensors." ACS applied materials & interfaces 8.39 (2016): 26407-26417. (Year: 2016).*

Khan, Mashooq et al., "Real-time liquid crystal-based biosensor for urea detection", Analytical Methods, vol. 6, Issue 15, Apr. 11, 2014 (pp. 5753-5759).

Stumpel, Jelle E. et al., "Stimuli-Responsive Materials Based on Interpenetrating Polymer Liquid Crystal Hydrogels", *Advanced Functional Materials*, vol. 25, Issue 22, Apr. 17, 2015 (pp. 3314-3320).

Noh, K.G et al., "Smart molecular-spring photonic droplets", Materials Horizons, vol. 4, Issue 4, Mar. 14, 2017 (8 pages in English).

International Search Report dated May 16, 2019 in counterpart International Patent Application No. PCT/KR2019/002039 (2 pages in English and 2 pages in Korean).

* cited by examiner

*Primary Examiner* — Robert J Yamasaki
(74) *Attorney, Agent, or Firm* — NSIP Law

(57) ABSTRACT

The present invention relates to a method for preparing a solid-state photonic crystal IPN composite functionalized with an enzyme, a photonic crystal IPN composite prepared by the method, and a biosensor using the photonic crystal IPN composite. The method of the present invention includes (1) mixing a nonreactive chiral dopant with a reactive nematic mesogen, curing the mixture, and removing the chiral dopant while maintaining a helical structure, to form a solid-state helical photonic crystal structure, (2) infiltrating a PAA hydrogel into the internal space of the photonic crystal structure, followed by curing to form an IPN-structured composite, and (3) immobilizing an enzyme in the IPN-structured composite. The PAA hydrogel is infiltrated into the solid-state helical photonic crystal structure and the enzyme is immobilized such that a pH change caused by the enzymatic reaction induces shrinkage and expansion of the PAA hydrogel, leading to a color change.

5 Claims, 14 Drawing Sheets

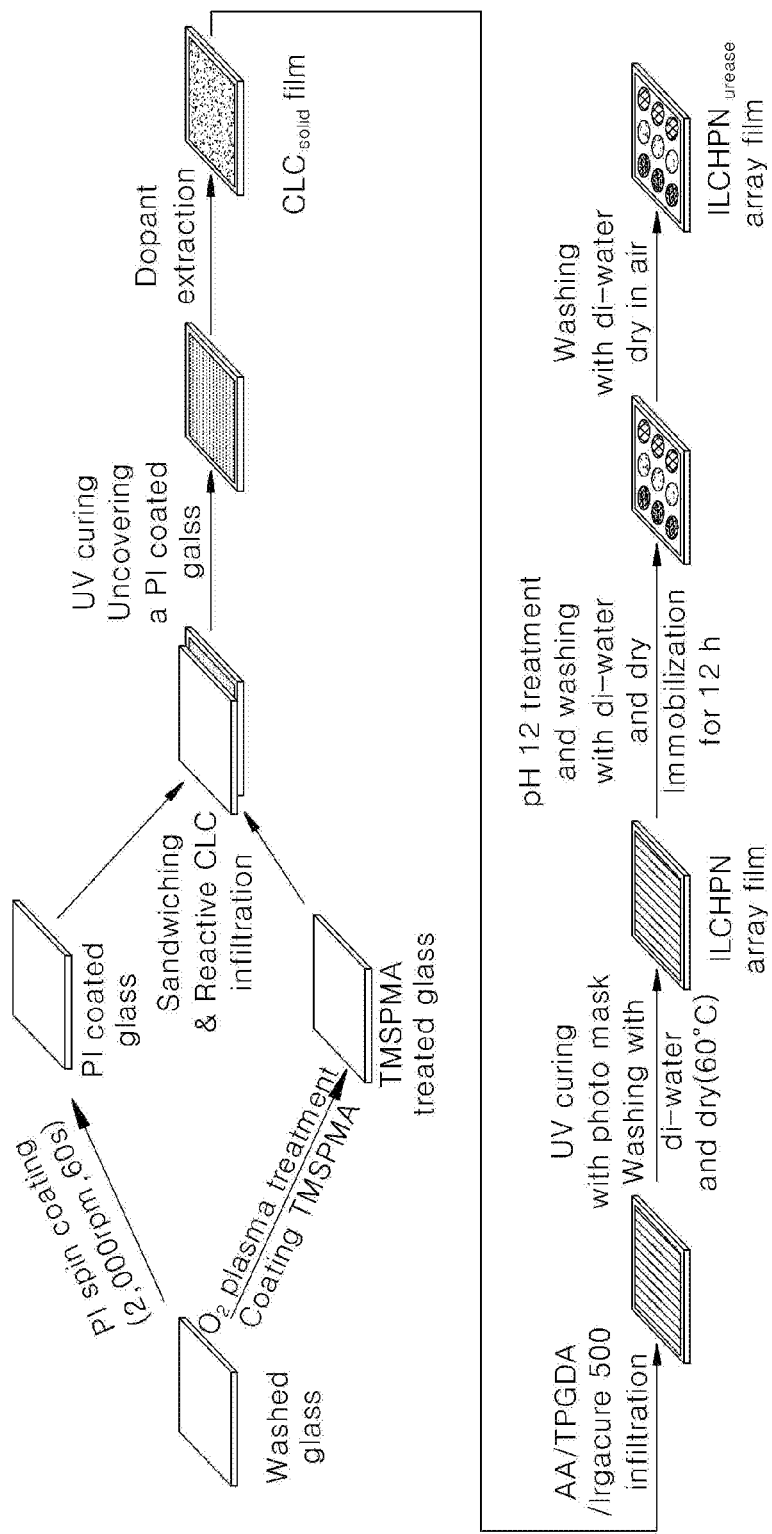
[Fig. 1]

[Fig. 2]
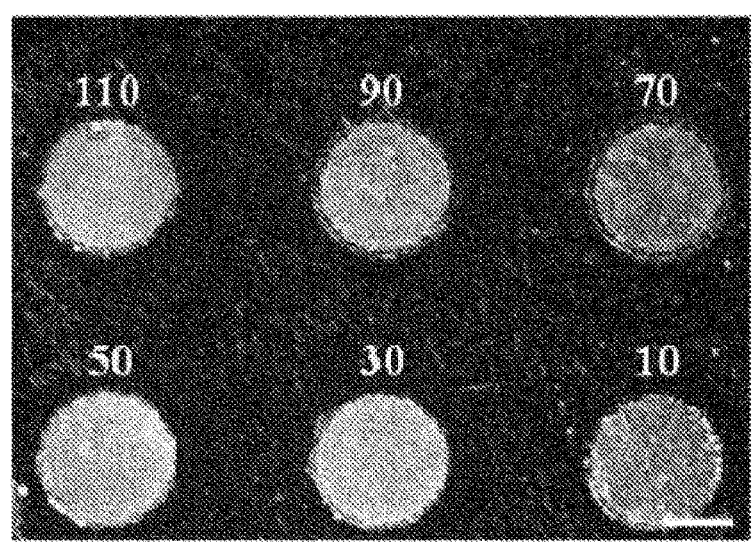

[Fig. 3]
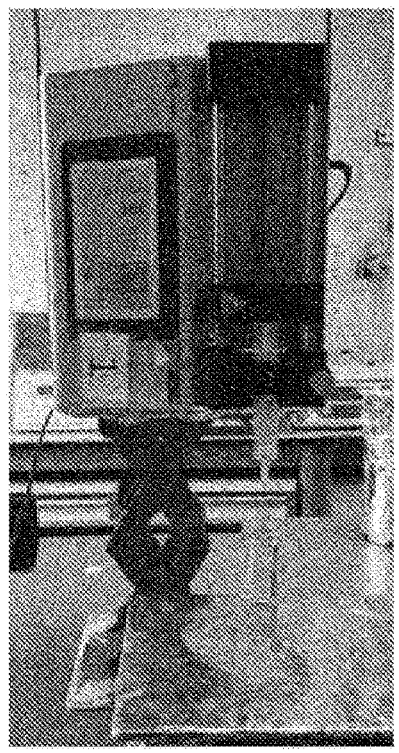 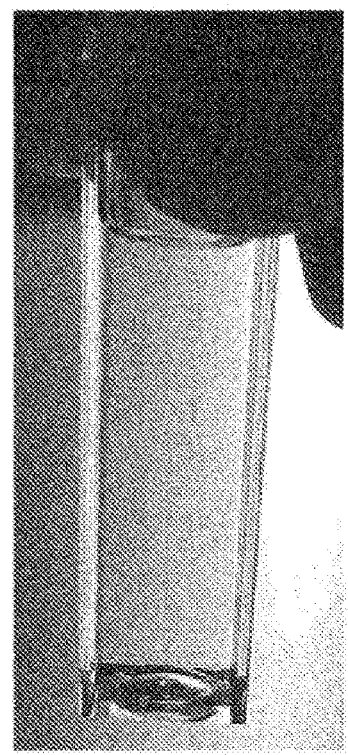
(a)          (b)

[Fig. 4]
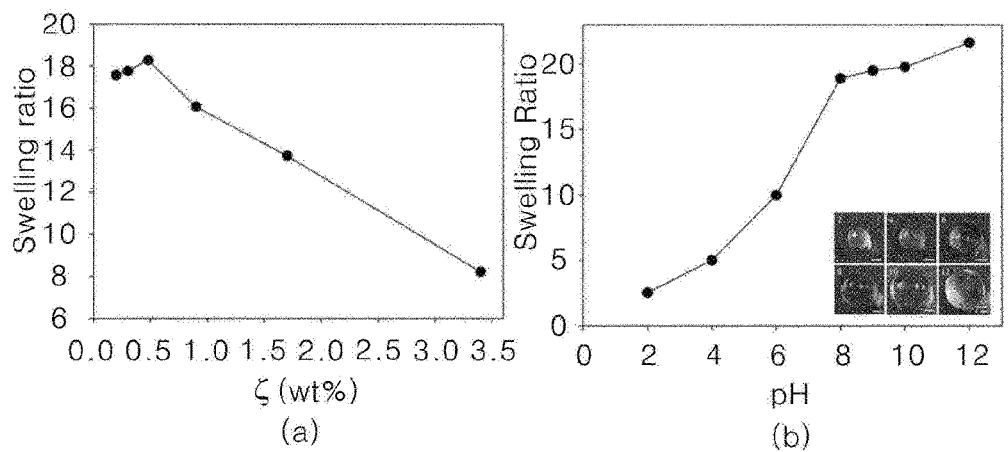

[Fig. 5]
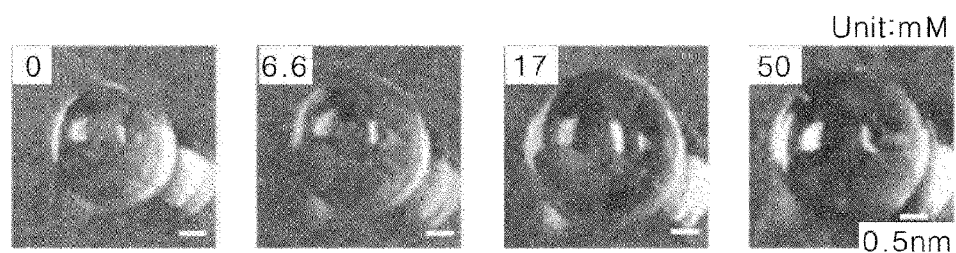

[Fig. 6]
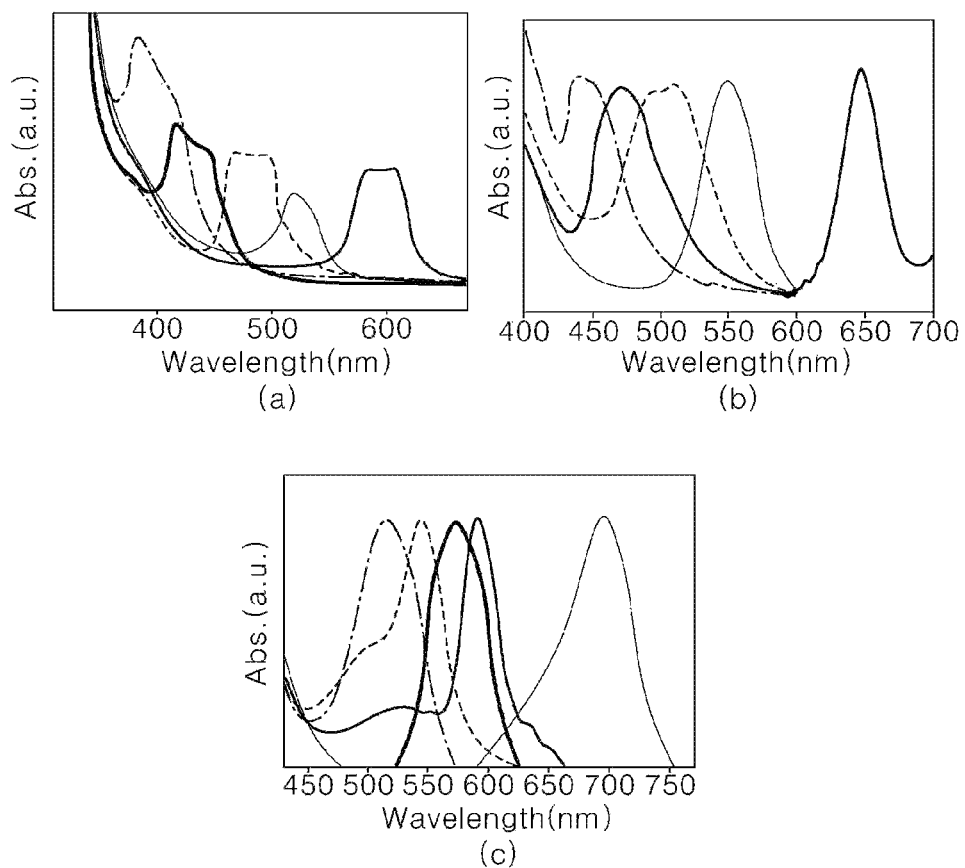

[Fig. 7]
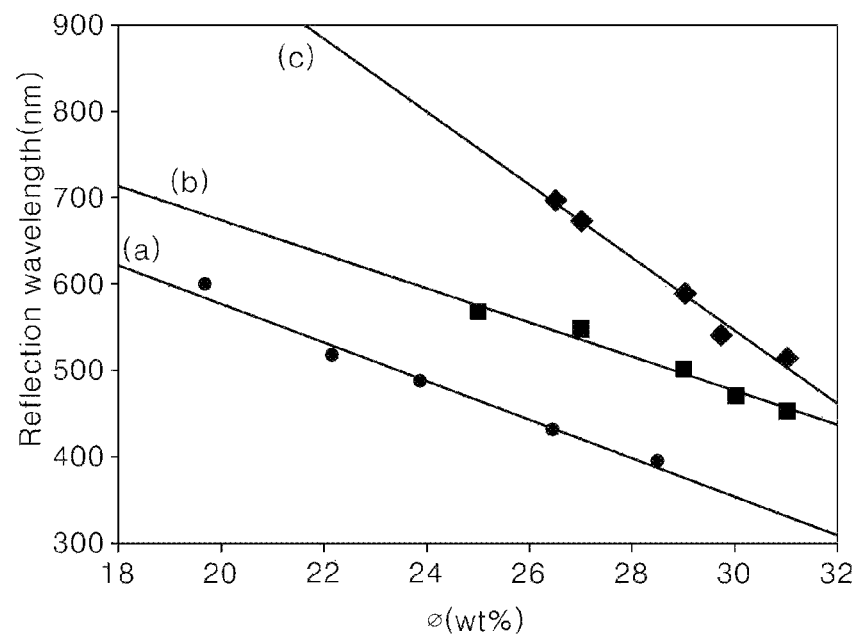

[Fig. 8]
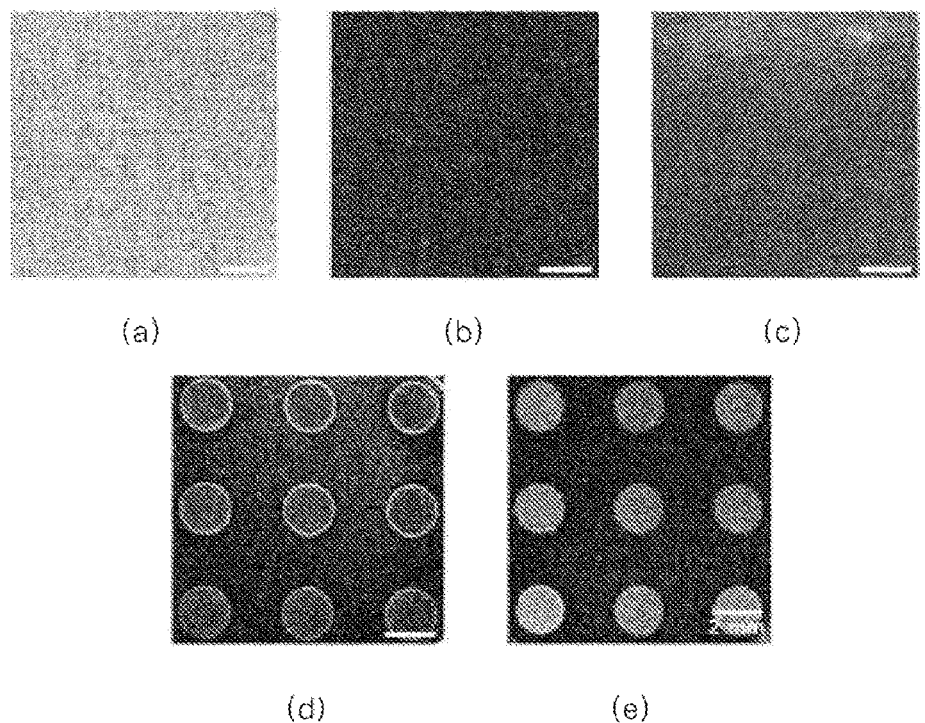
(a)　　　　　(b)　　　　　(c)
(d)　　　　　(e)

[Fig. 9]
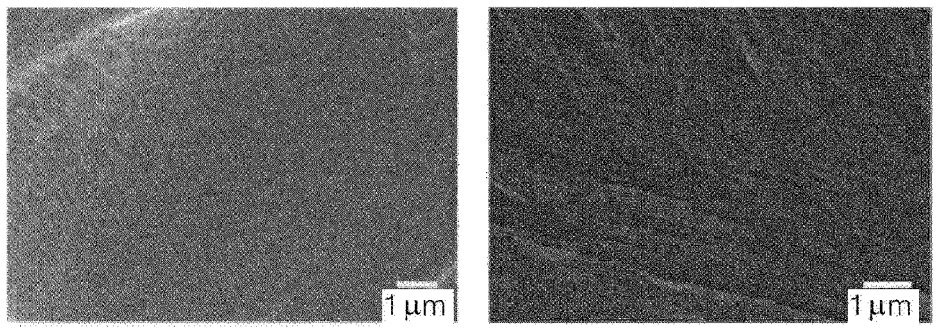
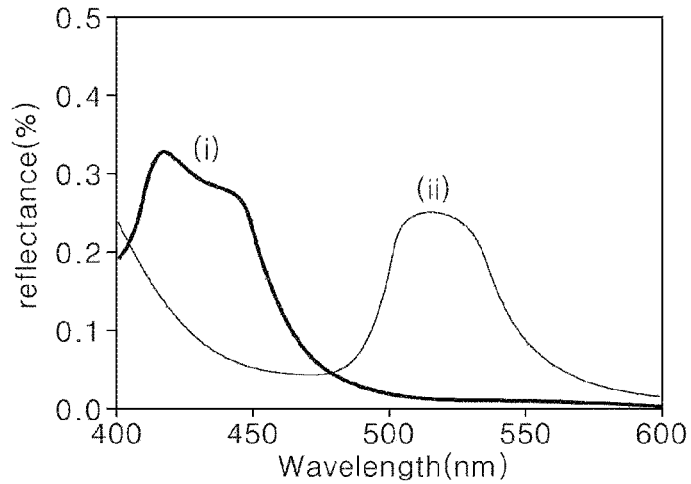
(c)

[Fig. 10]
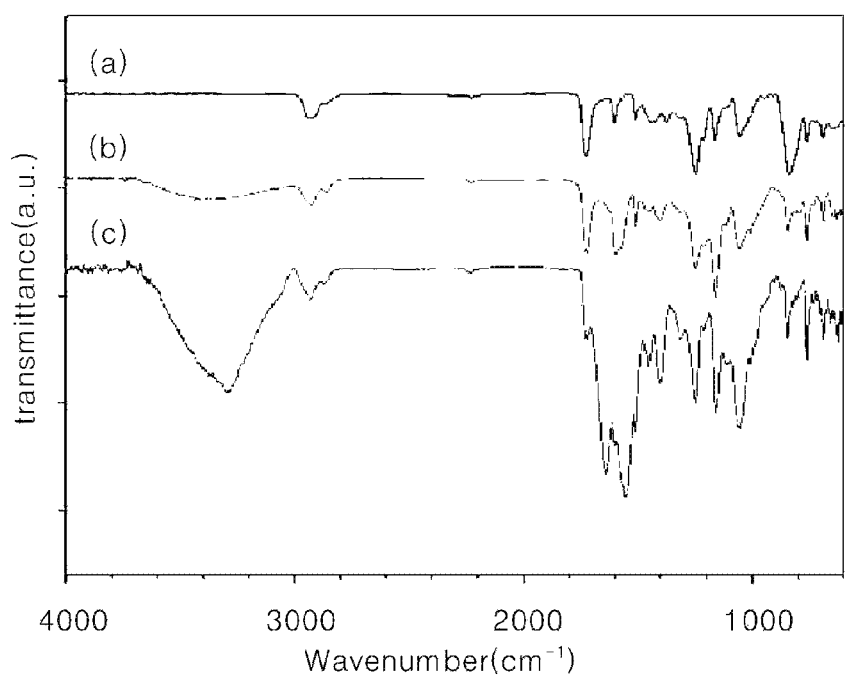

[Fig. 11]
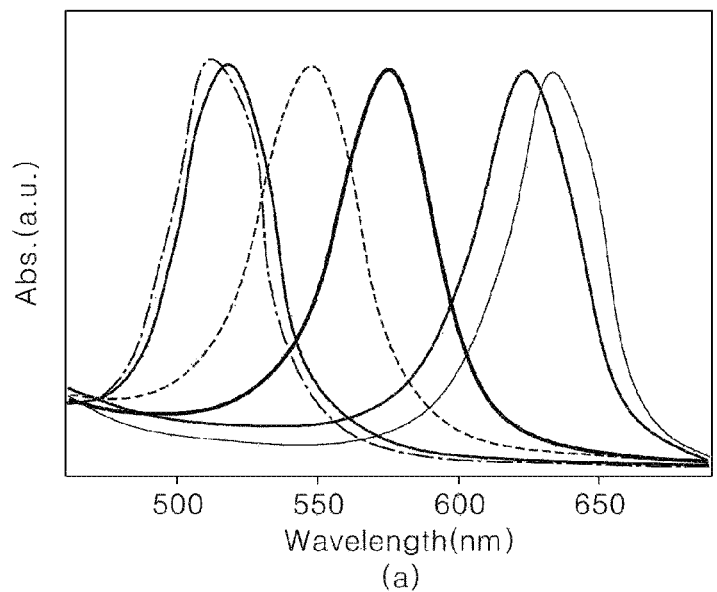
(a)
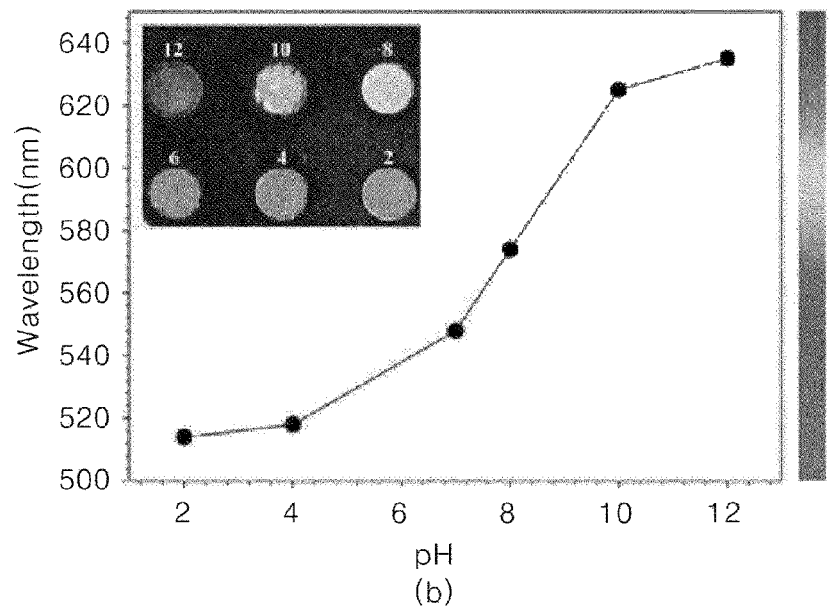
(b)

[Fig. 12]
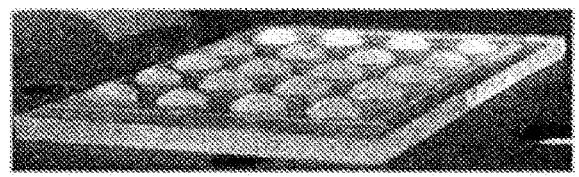
(a)
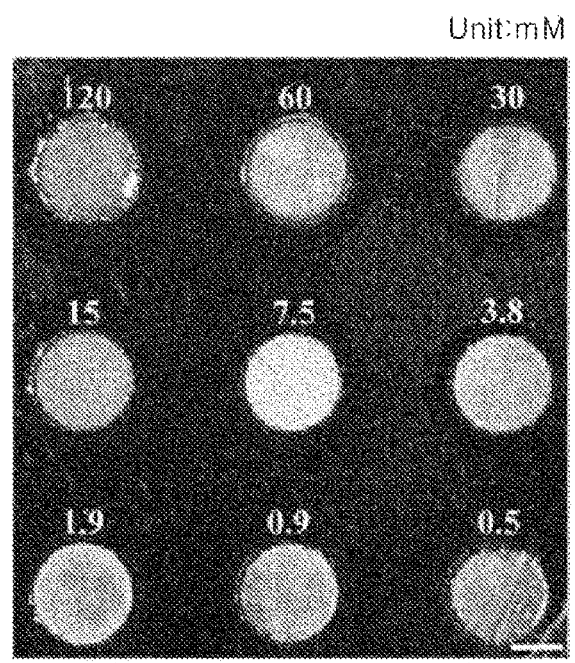
(b)

[Fig. 13]
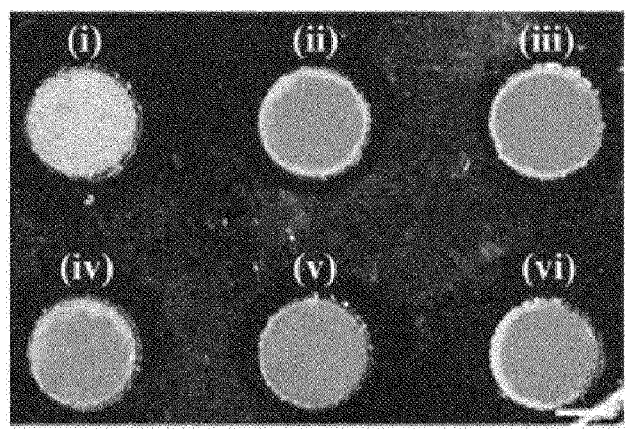
(a)
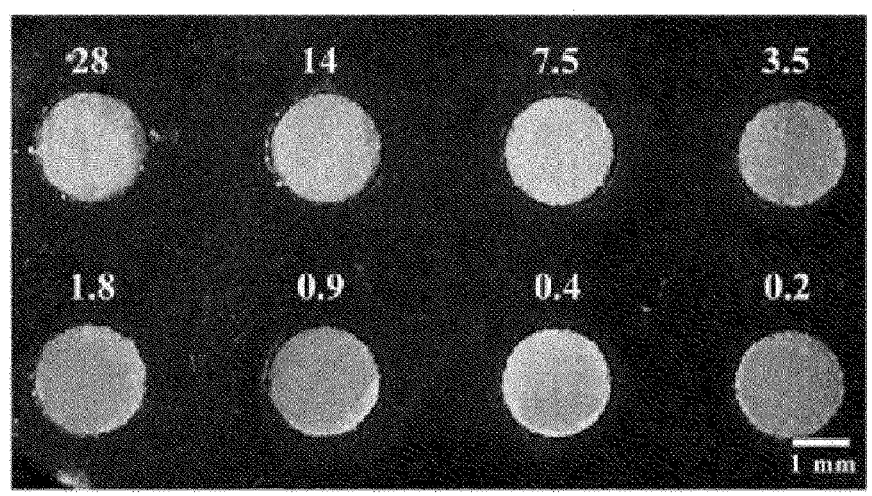
(b)

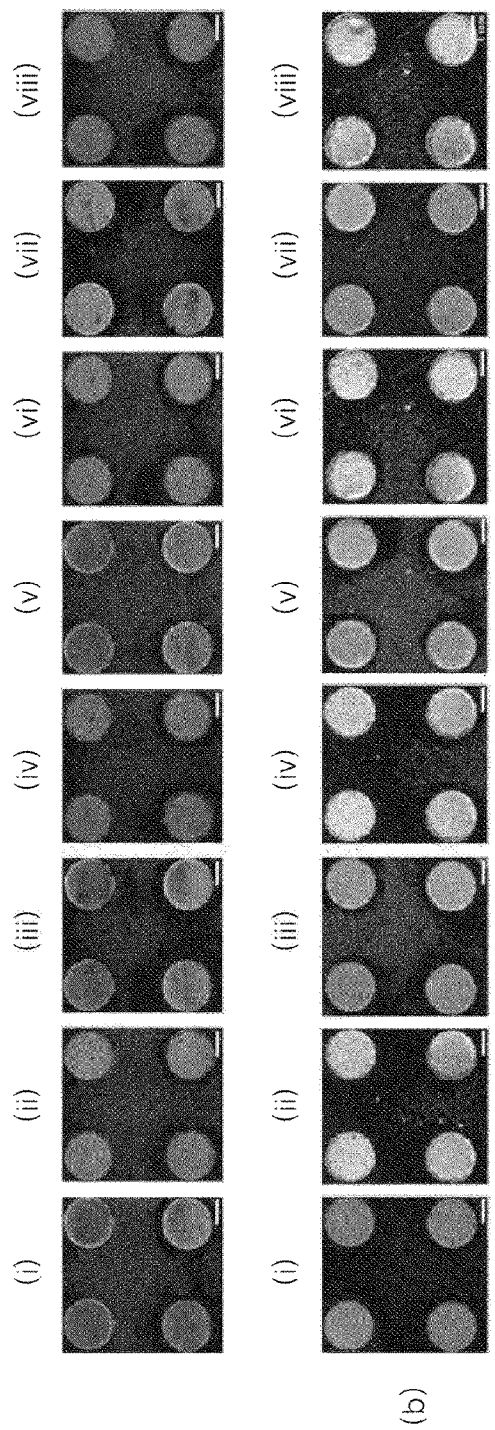
[Fig. 14]

METHOD FOR PREPARING SOLID-STATE PHOTONIC CRYSTAL IPN COMPOSITE FUNCTIONALIZED WITH ENZYME, PHOTONIC CRYSTAL IPN COMPOSITE PREPARED BY THE METHOD AND BIOSENSOR USING THE PHOTONIC CRYSTAL IPN COMPOSITE

CROSS REFERENCE TO RELATED APPLICATIONS

This application is a U.S. National Stage Application of International Application No. PCT/KR2019/002039, filed on Feb. 20, 2019, which claims the benefit under 35 USC 119(a) and 365(b) of Korean Patent Application No. 10-2018-0025203, filed on Mar. 2, 2018, in the Korean Intellectual Property Office, the entire disclosure of which is incorporated herein by reference for all purposes.

TECHNICAL FIELD

The present invention relates to a method for preparing a solid-state photonic crystal interpenetrating polymer network (IPN) composite functionalized with an enzyme, a photonic crystal IPN composite prepared by the method, and a biosensor using the photonic crystal IPN composite. More specifically, the present invention relates to a method for preparing a solid-state photonic crystal IPN composite functionalized with an enzyme in which a PAA hydrogel is infiltrated into a solid-state helical photonic crystal structure and an enzyme is immobilized such that a pH change caused by the enzymatic reaction induces shrinkage and expansion of the PAA hydrogel, leading to a color change.

BACKGROUND ART

Biosensors can be used for various applications, including medical, environmental, food, military, and industrial applications. However, currently available biosensor techniques require large amounts of samples to recognize target biomaterials. Further, these techniques are troublesome because they involve very complex processes for analyte loading, signal generation, signal amplification, complicated analysis of results, and incur considerable costs for application in daily life.

Under these circumstances, several sensor techniques with transducers functioned by electrochemical, optical, and mass detection methods have been employed for measuring small amounts of analytes with great precision. However, these techniques require complex sample preparation and expensive specialized equipment.

In this respect, optical sensors using photonic crystals capable of reflecting light at a certain wavelength have received much attention due to their ability to easily detect biomaterials and chemicals and visually detect analytes with color (or intensity) change without batteries.

Among photonic crystals, cholesteric liquid crystals (CLCs) exhibit a helically twisted molecular orientation resulting in special optical properties and have the advantage of their easy fabrication of the one-dimensional photonic structure.

The reflection wavelength of a cholesteric liquid crystal can be represented by Equation 1:

$$\lambda = n \times P \times \cos\theta \quad (1)$$

When a cholesteric liquid crystal is irradiated with unpolarized light, interaction of the helix structure with incident light of a selected wavelength will result in reflection of 50% of its intensity as circularly polarized light of a given handiness (left-handed or right-handed according to the handiness of the helix) while the other 50% are transmitted as circularly polarized light of the opposite handiness.

When the average refractive index (n) of a cholesteric liquid crystal material is constant, the reflection wavelength ($\lambda$) of the cholesteric liquid crystal depends on the pitch (P) of the helix. That is, cholesteric optical materials exhibit selective light reflection by the pitch of the helix to give unique reflection patterns. Thus, the CLC can be used as a sensor based on changes in the pitch upon exposure to external stimuli.

However, conventional CLCs in the form of liquid droplets have difficulty in maintaining their long-term stability.

The encapsulation of CLC droplets has been attempted to improve their stability. CLC droplets are easy to produce by encapsulating a liquid crystal on a polymer that serves as an emulsifier or binder for the liquid crystal, but the LC droplets remain in the liquid state and their size or distribution is difficult to control.

In view of this, the inventors have made an effort to provide a simple method for preparing a solid-state photonic crystal composite that can detect biomaterials by the naked eye through color changes without sophisticated instruments and can be stored for a long period of time. The present invention has been accomplished as a result of this effort.

DETAILED DESCRIPTION OF THE INVENTION

Problems to be Solved by the Invention

The present invention has been made in an effort to solve the above problems, and it is one object of the present invention to provide a method for preparing a solid-state photonic crystal IPN composite functionalized with an enzyme.

It is a further object of the present invention to provide a solid-state photonic crystal IPN composite functionalized with an enzyme prepared by the method.

It is another object of the present invention to provide a biosensor including the photonic crystal IPN composite.

Objects of the present invention are not limited to the above-mentioned objects, and those skilled in the art will clearly understand other unmentioned objects from the following description.

Means for Solving the Problems

A method for preparing a solid-state photonic crystal IPN composite functionalized with an enzyme according to one aspect of the present invention includes (1) mixing a non-reactive chiral dopant with a reactive nematic mesogen, curing the mixture, and removing the chiral dopant while maintaining a helical structure, to form a solid-state helical photonic crystal structure, (2) infiltrating a PAA hydrogel into the internal space of the photonic crystal structure, followed by curing to form an IPN-structured composite, and (3) immobilizing an enzyme in the IPN-structured composite.

A solid-state photonic crystal IPN composite functionalized with an enzyme according to a further aspect of the present invention is prepared by the method.

A biosensor according to another aspect of the present invention uses the solid-state photonic crystal IPN composite functionalized with an enzyme.

Effects of the Invention

The method of the present invention enables the preparation of a solid-state photonic crystal IPN composite functionalized with an enzyme in a simple and inexpensive manner by removing a chiral dopant from a cholesteric liquid crystal while preserving the unique helical structure of the cholesteric liquid crystal.

The IPN composite of the present invention has high selectivity depending on the immobilized enzyme and can detect multiple biomaterials. Due to these advantages, the IPN composite of the present invention is utilized as a biosensor for multiplexed detection.

In the biosensor of the present invention, a pH change caused by the enzymatic reaction induces expansion and shrinkage of the PAA hydrogel, leading to a color change that can be easily detected by the naked eye.

BRIEF DESCRIPTION OF THE DRAWINGS

FIG. 1 is a schematic diagram showing a method for preparing ICLCHPN$_{urease}$ according to one embodiment of the present invention.

FIG. 2 shows photographic images of 2×3 ICLCHPN$_{urease}$ prepared in Example 1, which were taken at predetermined time points after dropping 7.5 mM aqueous urea solution.

FIG. 3 shows the production of PAA hydrogel droplets: (a) a set-up for producing PAA hydrogel droplets; and (b) a produced PAA hydrogel droplet.

FIG. 4 shows the swelling ratios of PAA hydrogel droplets as functions of (a) the amount of a cross-linker and (b) pH.

FIG. 5 shows photographic images of PAA$_{urease}$ droplets in urea solutions at different urea concentrations.

FIG. 6 shows UV-Vis spectra of a dry CLC film, a dry ICLCHPN film, and a wet ICLCHPN film produced in Example 1.

FIG. 7 shows the reflection wavelengths of a dry CLC film, a dry ICLCHPN film, and a wet ICLCHPN film produced in Example 1.

FIG. 8 shows photographic images of a dry CLC film produced in Example 1 (a) before and (b) after dopant removal, (c) a dry ICLCHPN film produced in Example 1, (d) the dry ICLCHPN film after UV curing and removal of unreacted AA, and (e) a wet ICLCHPN film produced in Example 1 after UV curing and removal of unreacted AA.

FIG. 9 shows SEM images of fractured surfaces of CLC and ICLCHPN films produced in Example 1 and UV-Vis spectra of the films.

FIG. 10 shows FT-IR spectra of CLC, ICLCHPN, and ICLCHPN$_{urease}$ films produced in Example 1.

FIG. 11 shows UV-Vis spectra of an ICLCHPN film produced in Example 1 at different pH values and the wavelengths at the middle of the photonic band gap.

FIG. 12 shows photographic images of ICLCHPN$_{urease}$ films produced in Example 1: (a) a photographic image of a tilted 5×4 ICLCHPN$_{urease}$ film immediately after dropping aqueous urea solution; and (b) changes in the color of a 3×3 ICLCHPN$_{urease}$ film after dropping urea solutions with different concentrations.

FIG. 13 shows the selectivity and sensitivity of ICLCHPN$_{urease}$ films produced in Example 1: (a) photographic images showing color changes after various ingredients in blood were dropped on a 2×3 ICLCHPN$_{urease}$ film; and (b) photographic images showing color changes after human serum samples with different urea concentrations were dropped on a 2×4 ICLCHPN$_{urease}$ film.

FIG. 14 shows reversibility of ICLCHPN and ICLCHPN$_{urease}$ films produced in Example 1 in terms of pH and aqueous urea solution: (a) photographic images showing color changes after aqueous solutions at pH 2 and 12 were alternatingly dropped on a 2×2 ICLCHPN film; and (b) photographic images showing color changes after alternatingly washing a 2×2 ICLCHPN$_{urease}$ film with water and dropping aqueous urea solutions on the film.

MODE FOR CARRYING OUT THE INVENTION

The advantages and features of the present invention and methods for achieving them will become more apparent from the following embodiments that are described in detail below in conjunction with the accompanying drawings. However, the present invention is not limited to the illustrated embodiments and may be embodied in various different forms. Rather, the disclosed embodiments are provided so that the disclosure of the present invention will be thorough and complete, and will fully convey the scope of the invention to those skilled in the art to which the present invention pertains. The terminology used herein is for the purpose of describing particular embodiments only and is not intended to be limiting of the present invention. As used herein, the singular forms "a", "an" and "the" are intended to include the plural forms as well, unless the context clearly indicates otherwise.

Preferred embodiments of the present invention will be described in detail with reference to the accompanying drawings. Meanwhile, illustration and detailed description of the configuration, operation or effect that can be easily understood by those skilled in the art will be simplified or omitted, and only portions related with the present invention are shown.

One aspect of the present invention provides a method for preparing a solid-state photonic crystal IPN composite functionalized with an enzyme, including (1) mixing a nonreactive chiral dopant with a reactive nematic mesogen, curing the mixture, and removing the chiral dopant while maintaining a helical structure, to form a solid-state helical photonic crystal structure, (2) infiltrating a PAA hydrogel into the internal space of the photonic crystal structure, followed by curing to form an IPN-structured composite, and (3) immobilizing an enzyme in the IPN-structured composite.

A photonic crystal IPN composite prepared by the method of the present invention may be partially formed in a helical photonic crystal structure or may be individually distributed on a glass substrate.

Specifically, the method includes (1) mixing a nonreactive chiral dopant with a reactive nematic mesogen, introducing the mixture between two substrates stacked in parallel, curing the mixture, removing the upper substrate, and removing the chiral dopant while maintaining a helical structure, to form a solid-state helical photonic crystal film, (2) coating a PAA hydrogel mixture on the photonic crystal film to infiltrate the PAA hydrogel into the internal space of the photonic crystal film, followed by curing to form an IPN-structured composite, and (3) impregnating the IPN-structured composite with an aqueous enzyme solution and curing the composite to immobilize the enzyme in the composite. The resulting composite is in the form of a film.

The enzyme may be urease, glucose oxidase, cholesterol oxidase, horseradish peroxidase or creatinine deiminase.

The nonreactive chiral dopant may be selected from the group consisting of C15, CB15, CM21, R/S-811, CM44, CM45, CM47, R/S-2011, R/S-3011, R/S-4011, R/S-5011, and R/S-1011. (S)-4-cyano-4'-(2-methylbutyl)biphenyl (CB15) is preferably used as the nonreactive chiral dopant.

The reactive nematic mesogen may be selected from the group consisting of RM 82, RM 257, RM308, and RMM727. RMM727 is preferably used as the reactive nematic mesogen.

RMM727 refers to a mixture of a material including an acryloyloxy group, 1,6-hexamethylenediol diacrylate, and 2-methyl-1-(4-methylthiophenyl)-2-morpholinopropan-1-one. Reactive acryloyloxy mesogen APBMP, reactive acryloyloxy mesogen AHBCP, reactive acryloyloxy mesogen AHBMP or reactive acryloyloxy mesogen AHBPCHP may be used as the material including an acryloyloxy group.

A further aspect of the present invention provides a solid-state photonic crystal IPN composite functionalized with an enzyme prepared by the method.

The composite maintains a helical structure despite removal of the chiral dopant from the photonic crystal structure and exhibits the same light reflectivity as a cholesteric liquid crystal.

Thus, the solid-state photonic crystal IPN composite functionalized with an enzyme according to the present invention can be used as a sensor because its pitch is changed upon exposure to external stimuli, thus changing the reflection color that can be easily identified by the naked eye.

The biosensor detects a biopolymer based on the principle where a pH change caused by the enzymatic reaction ionizes carboxyl groups of the PAA hydrogel, the ionized carboxyl groups induce the repulsions between the chains, and the PAA hydrogel undergoes expansion and shrinkage due to the repulsions to induce expansion and shrinkage of the photonic crystal structure, resulting in a change in the wavelength range of the photonic band gap.

The wavelength range may be changed at a pH of 2 to 12.

The present invention will be explained in more detail with reference to the following examples. However, these examples are not intended to limit the scope of the present invention and should be construed as helping to understand the present invention.

Example 1

(1) Materials

RMM727 (reactive LC mixture, Merck, UK), (S)-4-cyano-4'-(2-methylbutyl)biphenyl (CB15, Synthon, Germany), acrylic acid (AA, Junsei, Japan), tri(propylene glycol)diacrylate (TPGDA, Sigma-Aldrich, USA), Irgacure 500 (photoinitiator, Ciba Inc., Swizerland), 3-(trimethoxysilyl) propyl methacrylate (TMSPMA, 98%, Sigma Aldrich, USA), poly(dimethylsiloxane) (PDMS, Sylgard© 184 Silicone elastomer kit, Dow Corning, USA), chloroform (Duksan, South Korea), acetone (Duksan, South Korea), polyimide (PI, Lixon Aligner, Chisso, Japan), NOA65 (Norland Products, USA), micro-pearl (Sekisui, Japan), N-hydroxysuccinimide (NHS, Sigma-Aldrich, USA), N-(3-dimethylaminopropyl)-N'-ethylcarbodiimide (EDC-HCl, Sigma-Aldrich, USA), pH buffer solutions (Samchun©, Korea), urea (Sigma-Aldrich, USA), urease (Sigma-Aldrich, USA), glucose (Sigma-Aldrich, USA), cholesterol (Sigma-Aldrich, USA), L-ascorbic acid (Sigma-Aldrich, USA), biotin (Sigma-Aldrich, USA), uric acid (Sigma-Aldrich, USA) and human serum (Sigma-Aldrich, USA) were used as-received. Deionized (DI) water was purified using a reverse-osmosis system (PureFO, Romax, Korea).

(2) Preparation of CLC Mixture Solution

Predetermined amounts of RMM727 and CB15 were mixed at 60° C. for 12 h via magnetic stirring. The ratio of RMM727 to CB15 is denoted as (D.

The transparent CLC mixture solution became milky after complete stirring and cooling to 25° C.

(3) Preparation of IPN-Structured Array Film Having IPN Structure Functionalized with Enzyme (ICLCHPN)

FIG. 1 is a schematic diagram showing a method for preparing $ICLCHPN_{urease}$ according to one embodiment of the present invention.

Referring to FIG. 1, a glass substrate (Marienfeld, Germany) was sequentially washed with methanol and deionized water and spin-coated with a PI aligner at 2,000 rpm for 60 s using a spin coater (SPIN-1200D, Midas, Korea). The PI-coated glass was rubbed by a rubbing machine (Namil Optical Components, South Korea). The PI-rubbed substrate can make CLC films globally oriented by planar anchoring and be easily removed after UV curing.

Another glass substrate was spin-coated with TMSPMA at 3000 rpm for 45 s using a spin coater and dried in an oven at 65° C. The coated glass substrate was used as a lower substrate that can react with the CLC mixture solution.

The two upper and lower substates were sandwiched with a thickness of 6 μm using a micro-pearl bonded by NOA65. The CLC mixture solution was inserted between the two sandwiched glasses by a capillary force. UV curing at 365 nm was performed with alternate 5-s sequences of turn-on and turn-off for 20 min using a UV curing machine (Innocure 100N, Lichtzen, South Korea).

The top substate was removed after the UV curing, and then the cured CLC film on the bottom substrate was washed 10 times with acetone to extract the chiral dopant.

A PAA hydrogel was infiltrated into the internal space of the CLC film by coating a mixture solution of AA/TPGDA/Irgacure 500 (98.5 wt %/0.5 wt %/1.0 wt %) on the CLC film for 30 min. The film was UV cured by exposing the UV light with a photomask for 10 min at a distance of 6 cm to form an IPN-structured composite film (hereinafter referred to as an "ICLCHPIN film"). The photomask contains dots with 2 mm diameter which are separated in a square way by 4 mm from the center of the dot.

The ICLCHPN film was activated by EDC/NHS at pH 12 by inserting it into the EDC/NHS aqueous solution (0.2 M/0.2 M) for 1 h. Urease was coupled by inserting the EDC-coupled ICLCHPN film into an aqueous urease solution (1 wt %), and then dried in open air to fabricate an IPN-structured composite film functionalized with urease (hereinafter referred to as an "ICLCHPNurease film").

FIG. 2 shows images of the 2×3 $ICLCHPN_{urease}$ film, which were taken at predetermined time points after dropping 7.5 mM aqueous urea solution. Referring to FIG. 2, the color was saturated after ≥75 min after dropping 7.5 mM aqueous urea solution on the dots of the 2×3 film.

(4) Fabrication of PAA Hydrogel Droplets

In order to confirm a change in the volume of PAA hydrogel droplets in Experimental Example 1 that follows, a mixture of TPGDA and acrylic acid (AA) monomers (AA/TPGDA mixture solution) was introduced into a vial containing a polydimethylsiloxane (PDMS) precursor with a syringe to fabricate droplets. When microfluidic PDMS (or glass capillary) was used, the droplets were merged when the in-situ UV curing is applied because the droplets become close each other in the tube due to increased density, leading to slow moving after cross-linking.

FIG. 3 shows the production of PAA hydrogel droplets: (a) a set-up for producing PAA hydrogel droplets; and (b) a produced PAA hydrogel droplet.

Referring to (a) of FIG. 3, AA/TPGDA droplets with 1 mm diameter were formed at the tip of the syringe with 0.3 mm diameter and introduced into a vial at a speed of 0.1 μl/s controlled by a syringe pump (LEGATO 100, kdScientific, USA). The syringe was moved vertically for making a series of droplets in PDMS. The produced PAA hydrogel droplets are almost stationary due to high viscosity of PDMS (51 poise).

As shown in (b) of FIG. 3, the stationary droplets in the vial were UV-cured without merging using a UV lamp (Innocure 100N, Lichtzen, South Korea) at a distance of 6 cm for 10 min. After UV curing, the PAA hydrogel droplets were picked up, washed with chloroform, and dried in an oven at 65° C. The PAA hydrogel droplet was activated by inserting it into the EDC/NHS aqueous solution (0.2 M/0.2 M) for 1 h. Urease was coupled by inserting the EDC-coupled PAA hydrogel droplet into the aqueous urease solution (1 wt %), and then dried in open air to fabricate a PAA droplet functionalized with urease (hereinafter referred to as a "$PAA_{urease}$ droplet")

(5) Analyzers

Cross-sectional images of the ICLCHPN film were obtained using a field-emission scanning electron microscope (FE-SEM, SU8220, Hitachi, Japan) that was operated at accelerating voltage of 15 kV. Specifically, the samples used for the FE-SEM were prepared by coating the cross-sectioned surfaces of the ICLCHPN film with platinum.

Fourier-transform infrared (FTIR) spectra were obtained with FTIR spectroscopy (FT/IR4100, Jasco, Japan) in the range of 600 to 4,000 cm$^{-1}$ at a resolution of 4 cm$^{-1}$ by collecting the average of 64 scans.

The UV-Vis spectra of CLC films in the range of 300-900 nm were obtained using a UV-vis spectrometer (UV-2401PC, Shimadzu, Japan) with the film oriented perpendicularly to the UV-vis beam.

Experimental Example 1

(1) Confirmation of Changes in the Volume of the PAA Hydrogel Droplets

In order to confirm changes in the volume of the PAA hydrogel droplets, the swelling behavior of the wet/dry PAA hydrogel droplets was analyzed as functions of the amount of the cross-linker and pH.

FIG. 4 shows the swelling ratios of the PAA hydrogel droplets as functions of (a) the amount of the cross-linker and (b) pH. Specifically, (a) shows the swelling ratios (Sr) of the PAA hydrogel droplets at pH 9 as a function of the amount (ζ) of the cross-linker TPGDA and (b) shows the swelling ratios of the PAA hydrogel droplets (ζ=0.5 wt %) at different pH values in vials. The insets in (b) are photographic images of the PAA hydrogel droplets at different pH values. The numbers in the upper left corners of the insets indicate pH values. The Sr is defined as $V/V_o$ where V and $V_o$ are volumes in wet and dry states, respectively.

Referring to (a) of FIG. 4, the swelling ratio tended to increase until ζ reached 0.5 wt %. The swelling ratio reached a maximum of 18.2 when ζ was 0.5 wt %, and thereafter, it decreased drastically with increasing ζ. When ζ was 0-0.5 wt %, the swelling ratio was a little bit low because of the incomplete cross-linked structure. The swelling ratio began to decrease from when ζ exceeded 0.5 wt %. The increased cross-linking density is believed to be responsible for the decreased swelling ratio.

Referring to (b) of FIG. 4, the swelling ratio was measured to be 2.6 when the pH in the vial containing the PAA hydrogel droplets was 2. The swelling ratio increased sharply until the pH reached 7, and thereafter, it increased steadily until the pH reached 12. The swelling ratio was 21.7 at pH 12.

From these results, it was found that the optimum concentration for the cross-linker TPGDA to induce the maximum swelling of the PAA hydrogel droplets was 0.5 wt % and the swelling increased as the pH increased although the highest swelling increase occurred at pH 7.

Immobilization of enzyme with EDC coupling gives the covalent bonds between enzyme and PAA hydrogel droplets.

FIG. 5 shows photographic images of the $PAA_{urease}$ droplets in urea solutions at different urea concentrations.

Referring to FIG. 5, the sizes of the $PAA_{urease}$ droplets were 2.15 mm, 2.37 mm, 2.63 mm, and 2.65 mm at urea concentrations of 0 mM, 6.6 mM, 17 mM, and 50 mM, respectively, indicating that the swelling of the $PAA_{urease}$ droplet increased as the urea concentration increased. The enzymatic reaction of urease with urea produces ammonia which is decomposed to the $NH^{4+}$ and $OH$ in water. Thus, it was found that the $PAA_{urease}$ droplets respond with enzymatic reaction of analytes.

(2) Confirmation of Structures of the ICLCHPN Films

UV-Vis spectra, photographic images, and SEM images of the ICLCHPN films were analyzed to confirm the structures of the films.

In this connection, (a), (b), and (c) of FIG. 6 are UV-Vis spectra of the dry CLC film, the dry ICLCHPN film, and the wet ICLCHPN film as a function of D, respectively. The wet ILCPHN film was in PBS buffer solution at pH 7.

In FIG. 7, (a), (b), and (c) show the reflection wavelengths of the dry CLC film, the dry ICLCHPN film, and the wet ICLCHPN film as a function of D, respectively. The wet ILCPHN film was in PBS buffer solution at pH 7.

Referring to FIGS. 6 and 7, the peak of the photonic band gap was clearly determined, indicating that the photonic structure was well developed before and even after infiltration and curing of the AA/TPGDA mixture solution in the CLC film. After infiltrating and curing the AA/TPGDA mixture solution in the CLC film, the reflection wavelength of the ILCPHN film increased due to the increased photonic band gap by the PAA.

The ratios of the reflection wavelength between before and after infiltration and curing for the dry ILCPHN film ($r_1$) were 1.17, 1.19, 1.22, 1.25, 1.29, and 1.34 at Φ=20, 22, 24, 26, 28, and 30 wt %. The calculated dopant volume % ($Φ_v$) were 22, 24, 26, 28, 30, and 32% at Φ=20, 22, 24, 26, 28, and 30 wt %. The $Φ_v$s were slightly higher than the (r1−1)×100, indicating that the space extracted by CB15 was almost filled with the AA/TPGDA mixture. The PAA hydrogel is hydrophilic and can be swelled by water. Thus, it is preferable that the initial state should be in the wet state.

The photonic band gap of the wet ILCPHN film increased as compared as to that of the dry ILCPHN film. Based on this, the reference color was chosen as green (λ=550 nm) at Φ=29.6 wt % for subsequent experiments because change from green to yellow and to red was more sensitive than other colors.

FIG. 8 shows photographic images of the dry CLC film (a) before and (b) after dopant removal, (c) the dry ICLCHPN film, (d) the dry ICLCHPN film after UV curing and removal of unreacted AA, and (e) the wet ICLCHPN film after UV curing and removal of unreacted AA.

(a) of FIG. 8 is a photographic image of the dry CLC film (Φ=29.6 wt %) before removal of CB15 and shows a bright green color. (b) of FIG. 8 is a photographic image of the dry CLC film (Φ=29.6 wt %) after removal of CB15 and shows a dark blue color. (c) of FIG. 8 is a photographic image of the dry ICLCHPN film and shows a bright blue color.

These results indicate that the uniform photonic structure was maintained all over the film after UV curing, dopant extraction, and AA/TPGDA infiltration. The observed colors (λ (bright green)=550 nm and λ (blue)=380 nm) from the CLC film before and after dopant extraction were consistent with the calculated data from the reported helical twist power of 9.86 μm$^{-1}$ (λ (bright green)=555 nm and λ (blue)=365 nm).

(d) of FIG. 8 is a photographic image of the dry ICLCHPN array film after UV curing with a photomask and removal of unreacted AA and shows sky blue dots with blue background. The sky blue dots were maintained after washing the unreacted AA due to cross-linked PAA after UV curing. However, the area other than dots returned to the blue colored background, indicating that the same photonic structure before AA/TPGDA mixture solution infiltration was returned by extraction of the AA/TPGDA mixture solution. (e) of FIG. 8 is a photographic image of the wet ICLCHPN array film after UV curing with a photomask and removal of unreacted AA. When the wet ILCPHN film was in PBS buffer solution at pH 7, the color of the reflection was changed to green.

The above results demonstrated the successful fabrication of the ICLCHPN array film with the CLC film.

FIG. 9 shows SEM images of fractured surfaces of the CLC and ICLCHPN films and UV-Vis spectra of the films. Specifically, (a), (b), and (c) of FIG. 9 are a SEM image of the cross-section surface of the CLC film when the film was cut perpendicular to the film surface, a SEM image of the cross-section surface of the ICLCHPN film when the film was cut perpendicular to the film surface, and UV-Vis spectra of the CLC and ICLCHPN films, respectively.

Referring to (a) of FIG. 9, a regular lamellar-like structure with a spacing of 190±5 nm was observed in the cross-section of the CLC film before infiltration of the AA/TPGDA mixture solution, indicating that the solid-state photonic structure was produced by UV curing and dopant extraction. The observed spacing represents p/2 where p is the pitch of the helix.

Referring to (b) of FIG. 9, a homogeneous lamellar-like structure was observed in the cross-sectional SEM image of the ICLCHPN film without deteriorating the regularity of the photonic structure while its spacing increased to 220±6 nm due to interpenetrated PAA network. No defects and phase-separated region were observed because of the infiltration of the AA/TPGDA mixture solution in the space of the dopant-extracted region. The solubility parameter of AA was 24 MPa$^{1/2}$ close to that of the cross-linked RMM727 (22 MPa$^{1/2}$), indicating that AA is a good solvent for a RMM727 so that the AA/TPGDA mixture solution can be easily infiltrated into the cross-linked RMM727.

Referring to (c) of FIG. 9, the perfect photonic band gaps were observed at 432 and 517 nm (the center of the peak) from the ILCPHN film (i) before and (ii) after infiltration and curing of the AA/TPGDA mixture solution, respectively. The flat region between bottom and upper edges of the photonic band gap indicates that the photonic structure is quite regular although the flatness before infiltration of the AA/TPGDA mixture solution is slightly deteriorated after UV curing.

The above results demonstrated that the ILCPHN array film having a good photonic structure could be prepared with the CLC film after infiltration of the PAA hydrogel.

(3) Confirmation of Structure of the ICLCHPN Film

The structure of the ICLCHPN$_{urease}$ film was confirmed using FT-IR spectroscopy.

In this connection, (a), (b), and (c) of FIG. 10 show FT-IR spectra of the CLC, ICLCHPN, and ICLCHPN$_{urease}$ films, respectively.

Referring to FIG. 10, the FT-IR spectrum of the CLC film ((a) of FIG. 10) shows —CH$_2$—, —CN, —C═O, —Ar—O— and —Ar— stretching bands at 2856 cm$^{-1}$, 2226 cm$^{-1}$, 1727 cm$^{-1}$, 1246 cm$^{-1}$, and 836 cm$^{-1}$, respectively. These peaks may be due to the mesogenic and spacer groups from RMM. The FT-IR spectrum of the ICLCHPN film ((b) of FIG. 10) showed the same peaks with the CLC film with other new peaks from PAA. Specifically, the new peaks appeared at 3400 cm$^{-1}$, 1408 cm$^{-1}$, and 1565 cm$^{-1}$, which are attributed to non-hydrogen bonded —OH stretching of the carboxylic acid group, symmetric, and antisymmetric stretching bands of the carboxylate ion (COO$^-$), respectively. The intensity of the —C—O— stretching of the carboxylic groups at 1158 cm$^{-1}$ became stronger than that of the CLC film because of the interpenetrated PAA. In addition to characteristic peaks of PAA, the C—O—C stretch peak of TPGDA appeared at 1010 cm$^{-1}$. These peaks indicate the presence of the IPN structure of PAA in the CLC film.

In the FT-IR spectrum of the ICLCHPN$_{urease}$ film ((c) of FIG. 10), peaks were observed at 1109 cm$^{-1}$, 1635 cm$^{-1}$, and 3290 cm$^{-1}$, which represent the —C—N stretching, C═O stretching (amide I), and —N—H deformation (amide II) bands from urease, respectively.

From the above results, it was found that urease was successfully immobilized in the ICLCHPN$_{urease}$ film.

(4) Confirmation of pH Responsiveness of the ICLCHPN Film

In order to confirm the pH responsiveness of the ICLCHPN film, UV-Vis spectra at different pH values were analyzed. The photonic bandgap at different pH values was analyzed with UV-Vis spectroscopy.

In order to use the ICLCHPN film as a biosensor with enzymes, it is important to confirm the pH responsiveness of the photonic bandgap prior to confirmation of the pH responsiveness of the ICLCHPN film. The swelling of the PAA droplet was continuously increased as the pH increased, as shown in FIG. 4. If the swelling of the PAA in the ICLCHPN film occurs in a similar way, the wavelength of the photonic bandgap would increase accordingly.

In this connection, FIG. 11 shows UV-Vis spectra of the ICLCHPN film at different pH values and the wavelengths at the middle of the photonic band gap.

(a) of FIG. 11 shows UV-Vis spectra of the ICLCHPN film at pH 2, 4, 6, 8, 10, and 12 from left to right. The photonic band gap was clearly observed and changed with respective to the pH.

(b) of FIG. 11 shows the wavelength at the middle of the band gap as a function of pH and photographic images of ICLCHPN array dots at different pH values. The numbers on the dots indicate pH. The wavelength of the band gap increased as the pH increased, while a large change was observed at pH≥8. This result indicates that deprotonation at high pH expands the PAA chains and accordingly increases the pitch of helix of the CLC film.

The maximum increase occurred at pH≥7 for the PAA droplet (see (b) of FIG. 4). The discrepancy of the maximum swelling may be owing to more hindrance of the expansion of the PAA in the interpenetrated CLC network than in the droplet.

The above results demonstrated that the photonic band gap of the ICLCHPN film was changed in response to pH.

Therefore, the ICLCHPN film is suitable for the enzymatic reactions causing local pH changes and can thus be applied to biosensors that can detect enzymes by the naked eye without sophisticated instruments.

(5) Confirmation of Enzyme Responsiveness of the ICLCHPN Film

In order to confirm the enzyme responsiveness of the ICLCHPN$_{urease}$ film, color changes after dropping the aqueous enzyme solution were observed.

From the results obtained in Experimental Example 1, it was found that the PAA$_{urease}$ droplets responded to the enzymatic reaction of urea. Thus, a urease reaction in the ICLCHPN$_{urease}$ film can increase the pH and accordingly expand the volume of the PAA by dropping the analyte solution on the dot of the array in the ICLCHPN so that the pitch (and reflection color) of the CLC in the ICLCHPN$_{enzyme}$ can be increased.

In this connection, FIG. 12 shows photographic images of the ICLCHPN$_{urease}$ film. (a) of FIG. 12 shows a photographic image of the tilted 5×4 ICLCHPN$_{urease}$ film immediately after dropping urea solution and (b) of FIG. 12 shows changes in the color of the 3×3 ICLCHPN$_{urease}$ film after dropping urea solutions with different concentrations. The numbers on the dots represent the concentrations of the urea solution.

Referring to (a) of FIG. 12, there were no crossings between the drops on the ICLCHPN$_{urease}$ array film owing to the hydrophobicity of the CLC film. For observation through optical microscopy (or the naked eye), the excess analyte solution was removed through a micropipette.

Referring to (b) of FIG. 12, the clear green dots changed to yellow ones after urea solution (3.5 µL) was dropped on the dots of the ICLCHPN$_{urease}$ film.

Specifically, green color did not change at the urea concentration was 0.5 mM and 0.9 mM; a mixed color of green and yellow appeared at 1.9 mM and 3.8 mM; the mixed color was changed to clear yellow color at 7.5 mM; and yellow color was changed to red at 15 mM.

On the other hand, the urea concentration in healthy human blood is 17-51 mg/dL for adult males and 13-44.6 mg/dL for females, so that the color of the ICLCHPN$_{urease}$ should be changed as a result of enzymatic reactions in samples containing urea at a maximum concentration of 45 mg/dL (7.5 mM) in order for the ICLCHPN$_{urease}$ to be used as a urea biosensor.

From the above results, it was found that the color change of the ICLCHPN$_{urease}$ film was strongly dependent on the concentration of urea and the ICLCHPN$_{urease}$ changed their color at a urea concentration of 7.5 mM. Thus, the ICLCHPN$_{urease}$ can be utilized as a urea biosensor for analyzing real blood.

(6) Evaluation of Selectivity and Sensitivity of the ICLCHPN Film in Human Serum In order to evaluate the selectivity and sensitivity of the ICLCHPN film to urea in human serum, urea was detected using ingredients in blood and serum×10 diluted with a PBS buffer solution.

First, ingredients present in real human blood were used for urea detection.

In this connection, FIG. 13 shows the selectivity and sensitivity of the ICLCHPN$_{urease}$ film. (a) of FIG. 13 shows color changes after various ingredients in blood were dropped on the 2×3 ICLCHPN$_{urease}$ film and (b) of FIG. 13 shows color changes after human serum samples with different urea concentrations were dropped on the 2×4 ICLCHPN$_{urease}$ film.

Referring to (a) of FIG. 13, changes in the color of the ICLCHPN$_{urease}$ film were observed after (i) urea (0.21 mg/mL), (ii) glucose (0.126 mg/mL), (iii) cholesterol (0.24 mg/mL), (iv) biotin (0.003 µg/mL), (v) ascorbic acid (0.017 mg/mL), and (vi) uric acid (0.006 mg/mL) were dropped on individual spots of array (volume of drop was 3.5 µL). Specifically, the color of the ICLCHPN$_{urease}$ array film was changed to a yellow color only after urea solution was dropped. In contrast, the color of the ICLCHPN$_{urease}$ array film was not changed after dropping the solutions of the other ingredients.

These results concluded that the ICLCHPN$_{urease}$ film has high selectivity to urea and can be used as a urea biosensor.

Next, human serum diluted with a PBS buffer solution was used for urea detection. Human serum is known to contain cholesterol, glucose, sodium, iron, proteins, endotoxin, and triglyceride. Urea with different concentrations was added to the diluted human serum.

The numbers in (b) of FIG. 13 indicate the concentrations of the urea solution. The green color of the ICLCHPN$_{urease}$ started to change to yellow when the concentration of the urea solution was 3.5 mM. The yellow color started to change to red at 14 mM and 28 mM. These results were similar to those of the urea aqueous solution in (b) of FIG. 12 indicating that many ingredients in blood did not interfere with the urea detection performance of ICLCHPN$_{urease}$.

Thus, ICLCHPN$_{urease}$ provides enough specificity for urea detection and can be used for real blood tests.

Reversibility of the ICLCHPN and the ICLCHPN$_{urease}$ array films was tested in terms of pH and urea solution.

In this connection, FIG. 14 shows reversibility of the ICLCHPN and ICLCHPN$_{urease}$ films in terms of pH and aqueous urea solution. (a) of FIG. 14 shows photographic images showing color changes after aqueous solutions at pH 2 and 12 were alternatingly dropped on the 2×2 ICLCHPN film. (b) of FIG. 14 shows photographic images showing color changes after alternatingly washing the 2×2 ICLCHPN$_{urease}$ film with water and dropping aqueous urea solutions on the film.

Referring to (a) of FIG. 14, the color of the ICLCHPN film was changed to sky blue after pH 2 aqueous solution was dropped and the sky blue color was changed to red after pH 12 aqueous solution was dropped. (i), (iii), (v), and (vii) are photographic images of the ICLCHPN film after pH 2 aqueous solution was dropped and (ii), (iv), (vi), and (viii) are photographic images of the ICLCHPN film after pH 2 and pH 12 aqueous solutions were alternatingly dropped. The color of the ICLCHPN film was alternatingly changed to sky blue and red until 4 cycles of dropping of pH 2 and pH 12 aqueous solutions, indicating that the reversible expansion and shrinkage of the PAA hydrogel in the ICLCHPN occurred by changing the pH of the aqueous solution.

Referring to (b) of FIG. 14, the color of the ICLCHPN film was changed to green after washing with water and the green color was changed to yellow after urea solution (3.5 µL, 7.5 mM) was dropped. (i), (iii), (v), and (vii) are photographic images of the ICLCHPN film after washing with water and (ii), (iv), (vi), and (viii) are photographic images of the ICLCHPN film after urea solution was dropped. The color of the ICLCHPN film was alternatingly changed to green and yellow until 4 cycles of washing and dropping, indicating that the ICLCHPN$_{urease}$ film can be reused several times by simple washing with water.

The foregoing has outlined rather broadly the features and technical advantages of the present invention so that those skilled in the art can better understand the claims that follow.

It will be understood by those skilled in the art that the invention can be implemented in other specific forms without changing the spirit or essential features of the invention. Therefore, it should be noted that the forgoing embodiments are merely illustrative in all aspects and are not to be construed as limiting the invention. The scope of the invention is defined by the appended claims rather than the detailed description of the invention. All changes or modifications or their equivalents made within the meanings and scope of the claims should be construed as falling within the scope of the invention.

The invention claimed is:

1. A method for preparing a solid-state photonic crystal IPN composite functionalized with an enzyme, comprising (1) mixing a nonreactive chiral dopant with a reactive nematic mesogen, curing the mixture, and removing the chiral dopant while maintaining a helical structure, to form a solid-state helical photonic crystal structure, (2) infiltrating a PAA hydrogel into the internal space of the photonic crystal structure, followed by curing to form an IPN-structured composite, and (3) immobilizing an enzyme in the IPN-structured composite.

2. The method according to claim 1, wherein the method comprises (1) mixing a nonreactive chiral dopant with a reactive nematic mesogen, introducing the mixture between two substrates stacked in parallel, curing the mixture, removing the upper substrate, and removing the chiral dopant while maintaining a helical structure, to form a solid-state helical photonic crystal film, (2) coating a PAA hydrogel mixture on the photonic crystal film to infiltrate the PAA hydrogel into the internal space of the photonic crystal film, followed by curing to form an IPN-structured composite, and (3) impregnating the IPN-structured composite with an aqueous enzyme solution and curing the composite to immobilize the enzyme in the composite and wherein the composite is in the form of a film.

3. The method according to claim 1, wherein the enzyme is urease, glucose oxidase, cholesterol oxidase, horseradish peroxidase or creatinine deiminase.

4. The method according to claim 1, wherein the nonreactive chiral dopant is selected from the group consisting of C15, CB15, CM21, R/S-811, CM44, CM45, CM47, R/S-2011, R/S-3011, R/S-4011, R/S-5011, and R/S-1011.

5. The method according to claim 1, wherein reactive nematic mesogen is selected from the group consisting of RM 82, RM 257, RM308, and RMM727.

* * * * *